(12) United States Patent
Youle et al.

(10) Patent No.: US 6,649,393 B1
(45) Date of Patent: Nov. 18, 2003

(54) MUTANT FORM OF CYTOTOXIC RIBONUCLEOLYTIC PROTEIN WHICH ALLOWS PRODUCTION BY RECOMBINANT METHODS

(75) Inventors: Richard J. Youle, Bethesda, MD (US); Veena M. Vasandani, Rockville, MD (US); Yon-Neng Wu, Bethesda, MD (US); Ester Boix, Barcelona (ES); Wojciech Ardelt, New City, NY (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1234 days.

(21) Appl. No.: 09/095,429

(22) Filed: Jun. 10, 1998

Related U.S. Application Data

(62) Division of application No. 08/626,288, filed on Apr. 4, 1996.

(51) Int. Cl.[7] .............................. C12N 9/22; C07H 21/04
(52) U.S. Cl. ............... 435/199; 435/252.33; 435/320.1; 536/23.2; 536/23.1; 536/23.5
(58) Field of Search .............................. 435/199, 252.3, 435/252.33; 424/94.1, 94.6; 536/23.2, 23.1, 23.5

(56) References Cited

FOREIGN PATENT DOCUMENTS

WO          WO 97/38112          10/1997

OTHER PUBLICATIONS

Creighton, T. E. "Protein Structure and Molecular Properties" second edition, W. H. Freeman and Company, New York, p. 57, 1993.*

Ardelt et al., *J. Biol. Chem.* 266:245–251 (1991).
Brinkman et al., *Biochimica et Biophysica Acta* 1198:27–45 (1994).
Creighton, T.E., in: *Proteins: Structures and Molecular Properties*, W. H. Freeman and Company (1993) pp. 9,62&63.
Darzynkiewicz et al., *Cell Tissue Kinet.* 21:169–182 (1988).
Louis et al., *Eur. J. Biochem.* 199:361–369 (1991).
Mikulski et al., *J. Natl. Canc. Inst.* 82:151–152 (1990).
Mikulski et al., *Cell Tissue Kinet.* 23:237–246 (1990).
Mikulski et al., *Int. J. Oncol.* 3:57–64 (1993).
Moolten et al., *Immunol. Rev.* 62:47–73 (1982).
Mosimann et al., *J. Mol. Biol.* 236:1141–1153 (1994).
Nambiar et al., *Eur. J. Biochem.* 163:67–71 (1987).
Newton et al., *J. Neurosci.* 14(2):538–544 (1994).
Newton et al., *J. Biol. Chem.* 267(27):19572–19578 (1992).
Rybak et al., *Drug Delivery* 1:3–10 (1993).
Youle et al., *Proc. Natl. Acad. Sci. USA* 91:6012–6016 (1994).

* cited by examiner

*Primary Examiner*—Nashaat T. Nashed
(74) *Attorney, Agent, or Firm*—Klarquist Sparkman, LLP

(57) ABSTRACT

The present invention provides recombinant Onc (rOnc) compositions and methods. Recombinant Onc proteins of the invention have an amino terminal methionine and comprise an Onc polypeptide. The amino terminal methionine of the protein allows for recombinant production in a bacterial host cell. Cleaving the amino terminal methionine exposes the amino terminal glutamine of the polypeptide. The Onc polypeptide has an amino terminal glutamine. Cyclization of the amino terminal glutamine of the polypeptide to a pyroglutamyl residue provides rOnc polypeptides and proteins have anti-cancer and anti-viral activity.

8 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 104 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:1:

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

(2) INFORMATION FOR SEQ ID NO:2:

(i) SEQUENCE CHARACTERISTICS:
       (A) LENGTH: 104 amino acids
       (B) TYPE: amino acid
       (C) STRANDEDNESS:
       (D) TOPOLOGY: linear (ii) MOLECULE TYPE: protein (ix) FEATURE:
       (A) NAME/KEY: Modified-site
       (B) LOCATION: 1
       (D) OTHER INFORMATION: /product= "OTHER"
           /note= "Xaa = pyroglutamic acid
(2-pyrrolidone-5-carboxylic acid or
           5-oxo-2-pyrrolidinecarboxylic acid)"

(xi) SEQUENCE DESCRIPTION: SEQ ID NO:2:

Xaa Asp Trp Leu Thr Phe Gln Lys Lys His Ile Thr Asn Thr Arg Asp
1               5                   10                  15

Val Asp Cys Asp Asn Ile Leu Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val

-continued

```
                        85                      90                      95
His Phe Val Gly Val Gly Ser Cys
                       100

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Ile Glu Gly Arg
1
```

MUTANT FORM OF CYTOTOXIC RIBONUCLEOLYTIC PROTEIN WHICH ALLOWS PRODUCTION BY RECOMBINANT METHODS

This is a division of application Ser. No. 08/626,288, filed Apr. 4, 1996.

FIELD OF THE INVENTION

The invention relates to methods and compositions for the recombinant production of Onc, a cytotoxic ribonucleolytic protein having anti-tumor and anti-viral properties. In particular, the invention relates to a recombinant Onc protein having an amino terminal methionine and comprising an Onc polypeptide.

BACKGROUND OF THE INVENTION

ONCONASE, or Onc, is a ribonuclease purified from *Rana pipiens* oocytes. While Onc is homologous to pancreatic RNases in amino acid sequence (Ardelt et al., *J. Biol. Chem.* 266:245–251 (1991)) and three dimensional structure (Mosimann et al., *J. Mol. Biol.* 236:1141–1153 (1994)), its pharmacological properties are quite unique. Onc displays cytostatic and cytotoxic activity against numerous cancer cell lines in vitro (Darzynkiewicz et al., *Cell Tissue Kinet.* 21:169–182 (1988)), is up to five-thousand times more toxic to animals than is the homologous protein, RNase A (Newton et al., *J. Neurosci.* 14(2):538–44 (1994)), and displays anti-tumor activity in vivo (Mikulski et al., *J. Natl. Canc. Inst.* 82:151–152 (1990); *Int. J. Oncol.* 3:57–64 (1993). Moreover, Onc has been found to specifically inhibit HIV-1 replication in infected H9 leukemia cells at non-cytotoxic concentrations (Youle et al., *Proc. Natl. Acad. Sci. USA* 91:6012–6016 (1994)). Such promising pharmacologic properties explain why this protein is currently the subject of phase III clinical trials.

Unfortunately, since Onc is isolated from oocytes, procurement of an adequate supply is uncertain. Recent concerns regarding the availability of the anti-cancer compound taxol illustrate some of the problems of obtaining natural products for use as pharmaceuticals. Similarly, availability of Onc is increasingly problematic in light of the declining population of *R. pipiens* and the seasonal variation in the supply of its oocytes.

Accordingly, what is needed in the art is a means to produce Onc by recombinant methods so as to meet demand for this therapeutic and alleviate the impact on its native source. Further, what is needed is a means to derivatize and alter the sequence of Onc to provide more efficacious compounds. Quite surprisingly, the present invention provides these and other advantages.

SUMMARY OF THE INVENTION

The present invention is directed to an rOnc protein, comprising a polypeptide of SEQ ID NO:1 or conservatively modified variant thereof. Preferably, the polypeptides of the invention have a glutamine residue at position +1 of the polypeptide. Even more preferably, the glutamine residue is at the amino terminus of the rOnc protein.

In one embodiment, the polypeptide comprises a hydrophobic residue at position 23. In a further embodiment, the polypeptide comprises the amino acid leucine at position 23. Preferably, the polypeptides of the present invention also have a lysine at position 9, a histidine at position 10, a histidine at position 97, a lysine at position 31, a phenylalanine at position 98, and a threonine at position 35.

In another embodiment, the amino acid sequence of rOnc protein is generally modified so that it is not susceptible to cleavage by cyanogen bromide. Preferably, upon cyclization of the amino terminal glutamine to pyroglutamyl, the polypeptide of SEQ ID NO:1 or conservative variants thereof have a relative $IC_{50}$ in U251 cells at least 50% that of the polypeptide of SEQ ID NO:2. Polypeptides of the present invention may be joined to a ligand binding moiety such as an immunoglobulin.

In another aspect of the present invention, a rOnc protein is provided. The rOnc protein comprises a polypeptide of SEQ ID NO:1 or conservatively modified variant thereof, preferably with a glutamine residue at position 1, and an amino terminal methionine. Nucleic acids encoding for the rOnc protein of the present invention are also provided. In a preferred embodiment, the amino terminal methionine is directly linked to the polypeptides of the present invention. The amino terminal methionine may also be linked to the polypeptides of the present invention via less than 50 amino acid residues.

In another aspect of the present invention, a method of making a rOnc protein is provided. The method comprises expressing in a host cell a nucleic acid encoding a rOnc protein comprising a polypeptide of SEQ ID NO:1 or conservatively modified variant thereof and an amino terminal methionine; cleaving the amino terminal methionine with a cleaving agent; and causing the glutamine residue at position 1 of SEQ ID NO:1 or conservative variant thereof to cyclize to a pyroglutamyl residue. In one embodiment, the nucleic acid encodes a hydrophobic residue at position 23 of the polypeptide. Preferably, the nucleic acid encodes a leucine at position 23 when the cleaving agent is cyanogen bromide. The cleaving agent is typically a peptidase or cyanogen bromide.

In another aspect of the present invention, a host cell is provided that expresses a nucleic acid coding for an rOnc protein. The rOnc protein comprises a polypeptide of SEQ ID NO:1 or conservatively modified variant thereof, and wherein the polypeptide has a glutamine at position 1; and an amino terminal methionine. An expression vector encoding a polypeptide of SEQ ID NO:1 or conservatively modified variant thereof, wherein the polypeptide has a glutamine at position 1, and an amino terminal methionine is also provided. In one embodiment, the expression vector encodes a leucine at position 23 of the polypeptide. In another, the expression vector encodes methionine or another hydrophobic residue at position 23 of the polypeptide.

The present invention has utility in providing a means to recombinantly produce rOnc for use as an anti-cancer, anti-tumor, and anti-viral composition. Additionally, the rOnc proteins of the present invention also have use as a cell culture selection agent against cancerous or tumorigenic cells thereby providing, for example, a means to select and identify gene therapy compositions which inhibit tumorigenic growth.

DESCRIPTION OF THE PREFERRED EMBODIMENT

Introduction

The present invention is directed to recombinant Onc (rOnc), a potent anti-tumor and anti-viral compound derived from P-30 Protein, an oocyte protein of *Rana pipiens* (Ardelt et al., *J. Biol. Chem.* 266:245–251 (1991)) and exemplified by the product ONCONASE, a registered tradename of the Alfacell Corporation, Bloomfield, N.J. The invention provides, inter alia, rOnc compositions, and compositions and methods for making rOnc.

The rOnc polypeptide of the present invention is altered in amino acid sequence relative to the native P-30 Protein (nOnc) such that recombinant production and subsequent conversion of this protein to its pharmacologically active form is readily achieved. Recombinant Onc has in vivo and in vitro utility. Recombinant Onc may be employed as an anti-cancer, anti-tumor, and anti-viral composition, or, for example, as a selection agent in cell culture work against tumorigenic cells. Thus, in some embodiments rOnc may be employed to inhibit HIV-1 replication, or to treat pancreatic cancer.

In contrast to homologous RNases, rOnc lacks appreciable ribonuclease activity or cytotoxicity when expressed with a methionine residue at the amino terminus. When chimeric proteins composed of rOnc and human pancreatic RNase (hRNase) sequences are constructed, they yield enzymes with similar substrate specificity and activity to that of Onc; however, they too lack appreciable cytoxicity. Thus, the features lending cytotoxicity to rOnc were not readily discernible. We have discovered that the amino terminal pyroglutamyl residue of rOnc plays a part in the cytotoxicity of this enzyme. Our identification of the role of this residue, and means to modify Onc for recombinant production while maintaining the desired cytotoxic activity provides, in part, the invention as described herein.

Definitions

Unless defined otherwise herein, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York), and Hale and Marham (1991) *The Harper Collins Dictionary of Biology*, Harper Perennial, N.Y. provide one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number-of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar-amino acids are well known in the art. Conservative modifications also include the deletion of 1, 2, 3, 4, 5, 6, or 7 amino acids from the carboxy end of SEQ ID NO:1 (extending to Histidine at position 97).

The "conservatively modified variants" of the polypeptides of the present invention are cytotoxic, as defined below, or alternatively, the "conservatively modified variants" are capable of forming a cytotoxic compound as a result of formation of an amino terminal pyroglutamyl residue. Those of skill will recognize that when the glutamine residue is the amino-terminal group in a peptide, polypeptide., or protein, it tends to spontaneously cyclize to pyrrolidone carboxylic acid (i.e., "pyroglutamyl") which is a particularly preferred form of the amino terminal glutamine residue.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

The terms "isolated" or "biologically pure" refer to material which is substantially or essentially free from components which normally accompany it as found in its naturally occurring environment. The isolated material optionally comprises material not found with the material in its natural environment. The rOnc proteins described herein are isolated and biologically pure since they are recombinantly produced in the absence of unrelated *Rana pipiens* proteins. They may, however, include heterologous cell components, a ligand binding moiety, a label and the like.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. A nucleic acid encodes another nucleic acid where it is the same as the specified nucleic acid, or complementary to the specified nucleic acid.

An "expression vector" includes a recombinant expression cassette which includes a nucleic acid which encodes a rOnc protein which can be transcribed and translated by a cell. A recombinant expression cassette is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter.

The term "recombinant" when used with reference to a protein indicates that a cell expresses a peptide, polypeptide, or protein (collectively "protein") encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

The term "subsequence" in the context of a particular nucleic acid or polypeptide sequence refers to a region of the nucleic acid or polypeptide equal to or smaller than the particular nucleic acid or polypeptide.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y. Generally, highly stringent wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman (1981) *Adv. Appl. Math*. 2: 482; by the homology alignment algorithm of Needleman and Wunsch (1970) *J. Mol. Biol*. 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

The term "substantial identity" or "substantial similarity" in the context of a polypeptide indicates that a polypeptide comprises a sequence with at least 70% sequence identity to a reference sequence, or preferably 80%, or more preferably 85i sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

One indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. However, nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule. Specific delivery typically results in greater than 2 fold, preferably greater than 5 fold, more preferably greater than 10 fold and most preferably greater than 100 fold increase in amount of delivered molecule (per unit time) to a cell or tissue bearing the target molecule as compared to a cell or tissue lacking the target molecule or marker.

The term "residue" as used herein refers to an amino acid that is incorporated into a polypeptide. The amino acid may-be a naturally occurring amino acid and, unless otherwise limited, may encompass known analogs of natural amino acids that can function in a similar manner as naturally occurring amino acids.

A "fusion protein" or when a molecule is "joined" to another refers to a chimeric molecule formed by the joining of two or more polypeptides through a peptide bond formed between the amino terminus of one polypeptide and the carboxyl terminus of another polypeptide. The fusion protein or the joined molecules may be formed by the chemical coupling of the constituent molecules or it may be expressed as a single polypeptide from a nucleic acid sequence encoding a single contiguous fusion protein. A single chain fusion protein is a fusion protein having a single contiguous polypeptide backbone.

A "ligand" or a "ligand binding moiety", as used herein, refers generally to all molecules capable of specifically delivering a molecule, reacting with or otherwise recognizing or binding to a receptor on a target cell. Specifically, examples of ligands include, but are not limited to, immunoglobulins or binding fragments thereof, lymphokines, cytokines, receptor proteins such as CD4 and CD8, solubilized receptor proteins such as soluble CD4, hormones, growth factors such as epidermal growth factor (EGF), and the like which specifically bind desired target cells.

"Cytotoxicity", as used herein, refers to the inhibition of protein synthesis in NIH 3T3 (ATCC No. CRL 1658) cells using the protocol described in Wu et al., *J. Biol. Chem.* 270:17476–17481 (1995). A cytotoxic protein of the present invention will have a relative 50% inhibitory concentration ($IC_{50}$) at least 20% that of an equimolar amount of the polypeptide of SEQ ID NO:2. More preferably, the relative $IC_{50}$ will be at least 30% or 40% that of the polypeptide of SEQ ID NO:2, and even more preferably, at least 50%, 60%, 70% or 80%.

As used herein, "hydrophobic" amino acid or residue refers to the natural amino acids: methionine, phenylalanine, leucine, isoleucine, or valine.

Numbering of Amino Acid Residues

The amino acid sequence positions described herein, unless otherwise indicated, use as a frame of reference the rOnc sequence of SEQ ID NO:1. Residues labeled with a negative ordinal number indicate the distance from the amino terminus of SEQ ID NO:1 in the direction increasingly distant from the carboxy terminus. It should be understood that position designations do not indicate the number of amino acids in the claimed protein per se, but indicate where in the claimed protein the residue occurs when the claimed protein sequence is aligned with SEQ ID NO:1. The amino acid sequence for SEQ ID NO:1 and for SEQ ID NO:2 are set forth below.

rOnc Proteins

The present invention includes rOnc proteins comprising a polypeptide of SEQ ID NO:1 or conservative variants thereof. The polypeptides of the present invention (SEQ ID NO:1 and conservative variants thereof) demonstrate cytotoxic activity, as defined herein. The rOnc proteins of the present invention may be limited to the polypeptide of SEQ ID NO:1 or conservative variants thereof, or may be inclusive of additional amino acid residues linked via peptide bond to the carboxy and/or amino terminus of the polypeptide. Preferably, the conservative variants of SEQ ID NO:1 comprise an amino terminal glutamine residue capable of spontaneous cyclization to a pyroglutamyl residue.

The polypeptide of SEQ ID NO:1 or conservatively modified variants thereof may have a leucine or other hydrophobic residue substituting for the methionine at position 23. Those of skill will recognize that a polypeptide lacking a methionine is typically not subject to specific cleavage using cyanogen bromide. The polypeptides of the present invention preferably have a lysine at position 9, a histidine at position 10, a lysine at position 31, a threonine at position 35, a histidine at position 97, or a phenylalanine at position 98, or combinations thereof.

Proteins of the present invention can be produced by recombinant expression of a nucleic acid encoding the polypeptide followed by purification using standard techniques. Typically, the rOnc proteins are encoded and expressed as a contiguous chain from a single nucleic acid. The length of the rOnc proteins of the present invention is generally less than about 600 amino acids in length.

Recombinant Onc proteins can also be synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Recombinantly produced or synthetic polypeptides can be condensed to form peptide bonds with other polypeptides or proteins formed synthetically or by recombinant methods. Various automatic synthesizers and sequencers are commercially available and can be used in accordance with known protocols. See, e.g., Stewart and Young (1984) *Solid Phase Peptide Synthesis*, 2d. ed., Pierce Chemical Co.

rOnc Proteins Comprising Amino Terminal Methionine

The present invention also includes rOnc proteins comprising: 1) a polypeptide of SEQ ID NO:1 or conservatively modified variant thereof, and 2) an amino terminal methionine. Isolated nucleic acids coding for the rOnc proteins of the present invention are also provided. Preferably, the amino terminal residue of the polypeptide is a glutamine. Various embodiments of the polypeptide of SEQ ID NO:1 and conservative variants thereof may be employed in this aspect of the invention.

Those of skill will understand that an amino terminal methionine or formlymethionine (collectively, "methionine") is typically required for protein synthesis in a bacterial host cell. The amino terminal methionine may be directly linked to the amino acid of position 1 of the polypeptides of the present invention via a peptide bond. Alternatively, the methionine is indirectly linked to the amino acid of position 1 of the polypeptides of the present invention via a plurality of peptide bonds from a contiguous chain of amino acid residues. The residues, extending and inclusive of the amino terminal methionine to the amino acid directly linked via a peptide bond to the amino terminal amino acid residue of the polypeptide, constitute an amino terminal peptide. Thus, the amino terminal peptide consists of all amino acid residues with a negative ordinal numbers linked to position +1 of SEQ ID NO:1 or conservatively modified variants thereof and has at its amino terminus a methionine residue. The amino terminal peptide is at least one amino acid residue in length (i.e., a methionine residue) or may be 5, 10, 20, 50, 100, 200, 300, 400, or more amino acids in length.

The amino terminal peptide may comprise a signal sequence for transport into various organelles or compartments of the host cell, or for transport into the surrounding media. The amino terminal peptide may also encode sequences which aid in purification such as epitopes which allow purification via immunoaffinity chromatography, or sequences recognized by endoproteases such as Factor Xa.

Making the rOnc Protein

The present invention is also directed to methods of making the rOnc polypeptides of SEQ ID NO:1 or conservative variants thereof. The polypeptides of the SEQ ID NO:1 or conservative variants thereof may conveniently be assayed for cytotoxicity or anti-viral (e.g., HIV-1) inhibition by methods disclosed herein.

A. Expression

The method comprises expressing in a host cell a nucleic acid encoding a polypeptide of SEQ ID NO:1 or conservative variant thereof, where the nucleic acid encodes an amino terminal methionine. Various embodiments of the polypeptides of the present invention previously described may be utilized in this aspect of the invention. By "host cell" is meant a cellular recipient, or extract thereof, of an isolated nucleic acid which allows for translation of the nucleic acid and requires an amino terminal methionine for translation of the nucleic acid into its encoded polypeptide. Eukaryotic and prokaryotic host cells may be used such as animal cells, bacteria, fungi, and yeasts. Methods for the use of host cells in expressing isolated nucleic acids are well known to those of skill and may be found, for example, in Berger and Kimmel, Guide to *Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). A variety of host cells and expression vectors are available from commercial vendors, or the American Type Culture Collection (Rockville, Md.). Accordingly, this invention also provides for host cells and expression vectors comprising the nucleic acid sequences described herein.

Nucleic acids encoding rOnc proteins can be made using standard recombinant or synthetic techniques. Nucleic acids may be RNA, DNA, or hybrids thereof. Given the polypeptides of the present invention, one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel; Sambrook et al.; and F. M. Ausubel et al. (all supra). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. Deoxynucleotides may be synthesized chemically according to the solid phase phosphoramidite triester method described by Beaucage and Caruthers (1981), *Tetrahedron Letts.*, 22(20) :1859–1862, e.g., using an automated synthesizer, e.g., as described in Needham-VanDevanter et al. (1984) *Nucleic Acids Res.*, 12:6159–6168.

One of skill will recognize many ways of generating alterations or variants of a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausubel, and Berger (all supra).

The nucleic acid sequences encoding the rOnc molecules or the fusion proteins may be expressed in a variety of host cells, including *E. coli*, other bacterial hosts, yeast, and various higher eukaryotic cells such as the COS, CHO and HeLa cells lines and myeloma cell lines. The recombinant nucleic acid will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors or plasmids of the invention can be transferred into the chosen host cell by well-known methods such as calcium chloride transformation for *E. coli* and calcium phosphate treatment, liposomal fusion or electroporation for mammalian cells. Cells transformed by the plasmids can be selected by resistance to antibiotics conferred by genes contained on the plasmids, such as the amp, gpt, neo and hyg genes.

Once expressed, the rOnc protein can be purified according to standard procedures of the art, including ammonium sulfate precipitation, column chromatography (including affinity chromatography), gel electrophoresis and the like (see, generally, R. Scopes, *Protein Purification*, Springer-Verlag, N.Y. (1982), Deutscher, *Methods in Enzymnology* Vol. 182: *Guide to Protein Purification.*, Academic Press, Inc. N.Y. (1990)).

B. Cleaving

After expression in the host cell, the resultant rOnc protein comprising an amino terminal methionine is treated with a cleaving agent or combination of cleaving agents. By "cleaving the amino terminal methionine" is meant cleaving the amino terminal methionine or amino terminal peptide from the polypeptides of SEQ ID NO:1 or conservative variants thereof. Thus, by "cleaving the amino terminal methionine", a polypeptide of SEQ ID NO:1 or conservative variant thereof is generated, optionally linked via peptide bonds to additional residues at the carboxy terminus.

The cleaving agent may be a proteolytic enzyme such as an exopeptidase or endopeptidase (collectively, "peptidase") or a chemical cleaving agent. Exopeptidases include aminopeptidase M (Pierce, Rockford, Ill.) which sequentially remove amino acids from the amino-terminus. Cleavage of the amino terminal methionine by exopeptidases may be controlled by modulating the enzyme concentration, temperature, or time under which the cleavage takes place. The resulting mixture may be purified for the desired protein by means well known to those of skill, for example, on the basis of length by electrophoresis. Endopeptidases useful for removing the amino terminal methionine and other residues of the amino terminal peptide include Factor Xa (Pierce) which cleaves at the carboxy side of Ile-Glu-Gly-Arg (SEQ ID NO:3) sequence. The chemical cleaving agent, cyanogen bromide, is conveniently employed to selectively cleave methionine residues.

The cleaving agent employed to cleave the amino terminal methionine will typically be chosen so as not to break a peptide bond within the polypeptide of SEQ ID NO:1 or conservative variants thereof. Alternatively, use of a particular cleaving agent may guide the choice of conservative substitutions of the conservative variants of the polypeptides of the present invention.

C. Cyclization

Upon cleavage of the amino terminal methionine and other residues of the amino terminal peptide, a protein comprising the polypeptide of SEQ ID NO:1 or a conservatively modified variant thereof is generated. The glutamine residue of SEQ ID NO:1 is caused to cyclize by any number of means, including spontaneously or by catalysis, to a pyroglutamyl residue. Spontaneous hydrolysis of amino terminal glutamine residues to their pyroglutamyl form is well known to the skilled artisan and its rate may be hastened by, for example, increasing the temperature. See, e.g., Robinson et al., *J. Am. Chem. Soc.*, 95:8156–8159 (1973). Cytotoxicity or anti-viral activity of the resultant rOnc protein may be assessed by means herein disclosed and well known to the skilled artisan.

Ligand Binding Moieties

The polypeptides and proteins of the present invention may also be joined via covalent or non-covalent bond to a ligand binding moiety. The rOnc molecule may be joined at the carboxy terminus to the ligand or may also be joined at an internal region as long as the attachment does not interfere with the respective activities of the molecules. Immunoglobulins or binding fragments thereof (e.g., single-chain Fv fragments) may conveniently be joined to the polypeptides of the present invention. Vaughan et al., Nature Biotechnology, 14:309–314 (1996).

The molecules may be attached by any of a number of means well-known to those of skill in the art. Typically the rOnc protein will be conjugated, either directly or through a linker (spacer), to the ligand. However, where both the rOnc and the ligand or other therapeutic are polypeptides it is preferable to recombinantly express the chimeric molecule as a single-chain fusion protein.

The procedure for attaching an agent to an antibody or other polypeptide targeting molecule will vary according to the chemical structure of the agent. Polypeptides typically contain a variety of functional groups; e.g., carboxylic acid (COOH) or free amine (—NH$_2$) groups, which are available for reaction with a suitable functional group on an. rOnc molecule to bind the other molecule thereto.

Alternatively, the ligand and/or rOnc molecule may be derivatized to expose or attach additional reactive functional groups. The derivatization may involve attachment of any of a number of linker molecules such as those available from Pierce Chemical Company, Rockford Illinois.

A "linkers", as used herein, is a molecule that is used to join two molecules. The linker is capable of forming covalent bonds to both molecules. Suitable linkers are well known to those of skill in the art and include, but are not limited to, straight or branched-chain carbon linkers, heterocyclic carbon linkers, or peptide linkers. Where both molecules are polypeptides, the linkers may be joined to the constituent amino acids through their side groups (e.g., through a disulfide linkage to cysteine).

A bifunctional linker having one functional group reactive with a group on a particular agent, and another group reactive with an antibody, may be used to form a desired immunoconjugate. Alternatively, derivatization may involve chemical treatment of the ligand, e.g., glycol cleavage of the sugar moiety of a glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptides, such as antibodies or antibody fragments, are also known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; 4,589,071; and Borlinghaus et al. Cancer Res. 47: 4071–4075 (1987), which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann, *Science*, 252: 1657 (1991), U.S. Pat. Nos. 4,545,985 and 4,894,443 which are incorporated herein by reference.

In some circumstances, it is desirable to free the rOnc from the ligand when the chimeric molecule has reached its target site. Therefore, chimeric conjugates comprising linkages which are cleavable in the vicinity of the target site may be used when the effector is to be released at the target site. Cleaving of the linkage to release the agent from the ligand may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Although the present invention has been described in some detail by way of illustration and example for purposes of clarity of understanding, it will be obvious that certain changes and modifications may be practiced within the scope of the appended claims.

EXAMPLE I

This example describes synthesis of rOnc and rhRNase.

The rOnc and human pancreatic ribonuclease (rhRNase) nucleic acids were synthesized using an *E. coli* codon bias (Grantham et al., *Nucleic Acids Res.* 9:r43–741981). Twelve oligonucleotides for assembling the synthetic rOnc and hRNase gene were synthesized on a CYCLONE PLUS DNA Synthesizer (Milligen-Biosearch) and purified using OPC cartridges (Applied Biosystems). Each oligonucleotide (20 mg) was then 5'-phosphorylated with KinAce-ItTM kit (Stratagene). Unincorporated rATP was removed using a Mermaid kit (BIO 101 Inc.). Appropriate oligonucleotide pairs (2 mg each) were annealed by incubation at 37° C. for 10 min. These oligonucleotides were then ligated together with DNA ligase at 16° C. overnight in a final volume of 200 ml. A 5 ml aliquot of the ligation mixture was subjected to PCR with a pair of primers designed to 1) incorporate restriction sites appropriate for cloning (Xba I and Bam HI at 5' and 3' ends of the sequence, respectively); 2) introduce a translation initiation codon immediately prior to the first nucleotide of the rOnc and hRNase nucleic acid sequence; and 3) incorporate tandem translation termination codons immediately after the last nucleotide of the final codon. The amplified PCR products were then cloned into pET-11d plasmid (Novagen) under the control of a strong bacteriophage T7 promoter using Xba I and Bam HI restriction sites, and sequenced. The final sequences were those desired to generate the rOnc and hRNase protein lacking the leader sequence and having an additional, N-terminal, Met-(−1) residue.

Mutant rOnc and rOnc-hRNase hybrids were constructed using PCR with appropriate primers and rOnc or hRNase DNA as templates. The following constructs were synthesized and cloned, and confirmed by nucleic acid sequencing: Met(−1)-rOnc (Lys9 to Gln substitution), Met(−1)-rOnc (Gln1, Met23 to Leu substitution), $rOnc_{1-9}$-$hRNase_{12-127}$hybrid and $rhRNase_{1-11}$-$rOnc_{10-104}$hybrid.

EXAMPLE II

This example describes the expression of rOnc and rhRNase.

The rOnc, rhRNase, and hybrid nucleic acids of Example I were expressed in BL21(DE3) *E. coli* cells (Novagen) with isopropyl-1-thio-β-galactopyranoside (IPTG) as the inducing agent. The fraction of inclusion bodies that contain the expressed protein was isolated and treated as described (Wu et al., *J. Biol. Chem.* 270: 17476–17481 (1995)). The expressed protein represented more than 70% of the total inclusion body protein. The inclusion bodies were vigorously washed, the proteins denatured with 6 M guanidine-HCl containing 0.1 M reduced glutathione, and incubated at room temperature under nitrogen for 2 hours. The proteins were then renatured by rapid dilution into a Tris-Acetate buffer containing 0.5 M L-arginine and 8 mM oxidized glutathione, and incubated at 10° C. for at least 24 hours. The refolded ribonucleases were then purified by cation exchange chromatography on S-Sepharose. The S-Sepharose column was eluted with a linear sodium chloride gradient (0–0.5 M) in 0.15 M sodium acetate buffer, pH 5.0. The main peak was collected and concentrated by ultrafiltration and rechromatographed by size exclusion on Sephacryl S-100 in 0.075 M ammonium bicarbonate, and then lyophilized. Protein concentration of recombinant proteins was determined using the BCA protein microassay reagent (Pierce) using RNase A (bovine pancreatic) as a standard, and spectrophotometrically at 278 nm for RNase A (e278 =9800 M−1cm−1) and at 280 nm for rOnc (extinction coefficient 1=8.8). The homogeneity of the purified proteins was checked by 10–27% SDS-polyacrylamide gel electrophoresis. The typical yield for all RNases was 10–50 mg of purified recombinant protein per liter of culture.

EXAMPLE III

This example describes cyanogen bromide treatment and purification of the cleaved protein rOnc (<E1, M23L).

CNBr cleavage of Met-(−1) residue of Met(−1)-rOnc was carried out as described by Gross & Witkop (*J. Biol. Chem.* 237: 1856–1860 (1962)) with a few modifications. A 100-fold molar excess of CNBr to the protein was used in the reaction and low molecular weight products generated were removed by extensive dialysis against 0.1 M Tris, pH 7.5. The efficiency of the CNBr treatment was estimated to be about 50%.

After the CNBr treatment, to separate the cleaved and the uncleaved forms, the treated protein was loaded on a Mono S cation exchange column, equilibrated in 50 mM MES pH 6.75, buffer, and the proteins were eluted with a linear gradient of NaCl from 0 to 0.15 M. Fractions of 1 ml were collected and assayed for activity against RNA. A peak of maximum activity was eluted at the beginning of the gradient. The fractions corresponding to this peak were pooled and concentrated. The purified protein was checked by 10–27% sodium dodecyl sulfate-polyacrylamide gel electrophoresis (SDS-PAGE). The cleavage of the Met(−1) residue was confirmed by determination of the protein mass before and after cleavage by matrix assisted laser desorption ionization:(MALDI) using a sinapinic acid matrix. To obtain more accurate masses, apomyoglobin was used as an internal standard. Mass values of 11948 for Met−1 rOnc (Q1, M23L) and 11799 for rOnc (<E1, M23L) were found, which differ by less than 2 from the expected values (11949.9 and 11801.66 Daltons, respectively). Cleavage and cyclization of the protein was checked by the N-terminal sequencing, further confirming that the Gln1 residue cyclized to block the N-terminus. Parenthetical nomenclature describes the alterations to the native Onc sequence using the single-letter amino acid code. "<E" refers to a pyroglutamyl residue and the number following the letter indicates the position of the residue from the amino terminal end (i.e., the +1 position). The letter directly following a number indicates the substituting residue. Thus, for M23L, leucine is a substitution for the methionine at position 23.

EXAMPLE IV

This example describes assays for ribonuclease activity.

Onc was purified from the eggs of *Rana pipiens* by a modification of the method of Ardelt et al. *J. Biol. Chem.*, 266: 245–251 (1991). Cytidine 2',3'-cyclic phosphate (C>p), cytidylyl-3', 5'-adenosine (CpA), uridylyl-3', 5'- guanosine (UpG), poly(cytidylic acid) (poly(C)), poly(uridylic acid) (poly(U)) and yeast RNA were used as substrates, and the kinetic parameters were determined by a spectrophotometric assay. Activity of hydrolysis of C>p to 3'-CMP was measured by recording the increase in absorbance at 296 nm, and the transesterification activity for dinucleotides and polynucleotides was followed by the decrease in absorbance at 280 nm for UpG and poly(U), 286 nm for CpA, 294 nm for poly(C), and 300 nm for yeast RNA. For yeast RNA, at low substrate concentrations, the increase at 260 nm was also followed.

Substrate concentration ranges were 0.05–2 mM for C>p, UpG and CpA, and 0.02–2 mg/ml for poly(C), poly(U) and yeast RNA. Final enzyme concentrations were in the range of 1–80 nM for hRNase and RNase A; 0.5–2 mM for rOnc$_{1-9}$-hRNase$_{2-127}$; 2–15 mM for rhRNAse$_{1-11}$-Onc$_{10-104}$; and 10–60 mM for native Onc, rOnc (>E1, M23L), and rOnc (K9Q), depending on the activity of the enzyme assayed for each substrate. All assays were carried out in 0.2 M sodium acetate, pH 5.5, or Tris 0.1 M, NaCl 0.1 M, pH 7.5, at 25° C. For ionic strength studies, yeast RNA and Tris 20 mM, pH 7.5, were used, and NaCl was increased gradually from 0 to 150 mM; the relative initial velocity was calculated under conditions of [S] <<Km. 1 cm path length cells were used for C>p and 0.2 cm path length cells were used for CpA, UpG, poly(U), poly(C) and yeast RNA. Kinetic parameters, Km and kcat were obtained by the nonlinear regression data analysis program ENZFITTER (Leatherbarrow, "Enzfitter: a non-linear regression data analysis program for the IBM-PC", Elsevier Biosoft, Cambridge (1987)).

Kinetics

Table 1 shows the kcat values relative to rhRNase activity. For long-chain substrates, the relative Vmax/[Eo] instead of kcat was calculated, as substrate concentration was calculated in mg/ml. The values in Table 1 are the averages of 2–3 determinations, with a standard error of less than 10%. Poly(C)/poly(U) ratio were calculated in each case from the absolute Vmax/[Eo] values.

The buffers used for comparison of RNase activity with different substrates in Table 1 have ionic strengths around the optimum activity for hRNase and hybrid proteins, whereas the Onc optimum is at much lower ionic strength. However, we have chosen these buffer conditions in the kinetic analysis because they are standardly used in the literature, and they are closer to physiological conditions. Even if Onc is not studied at its optimal ionic strength, the activity of Onc at low or high ionic strength is still significantly much lower than any of the hRNase or hybrid activity values in the whole ionic strength range. The N-terminal amino acid residue appears to have an important role in the active site of Onc and not in hRNase. To further explore the exceptional role of the pyroglutamyl residue in Onc enzyme activity and cytotoxicity we exchanged the N-terminus of hRNase with that of Onc. We made the complementary exchange of the Onc N-terminus onto hRNase, however, the Onc pyroglutamate was not reconstituted. The enzyme kinetic analysis of Onc-hRNase hybrids highlights the importance of the N-terminal a helix in the active center and in the catalytic efficiency and substrate specificity of the enzymes. The substitution of residues 1–11 of hRNase with residues 1–9 of Onc (rOnc$_{1-9}$-hRNase$_{12-127}$) lowers the activity to 0.1 to 10% relative to that of hRNase depending on the substrate assayed (Table 1). The rOnc$_{1-9}$-hRNase$_{12-127}$ hybrid maintains the preference for poly(C) seen in hRNase, however the poly (C)/ poly(U) ratio is decreased from 16 to 6 (Table 2).

TABLE 1

Relative catalytic activity (%) of hRNase; nOnc and Onc-hRNase Hybrids

| | C > p | CpA | UpG | yeast RNA | poly(C) | poly(C) | poly(U) | poly(U) |
| --- | --- | --- | --- | --- | --- | --- | --- | --- |
| rhRNase | 100 | 100 | 100 | 100 | 100 | 100 | 100 | 100 |
| RNase A | 139 | 205 | 910 | 825 | 78 | 40 | 68 | 90 |
| rOnc$_{1-9}$-hRNase$_{12-127}$ | 2.7 | 1 | 11.7 | 5.5 | $2.9 \times 19^{-1}$ | $1.2 \times 10^{-1}$ | 1.2 | 1.1 |
| rhRNase$_{1-11}$-Onc$_{10-104}$ | $1 \times 10^{-1}$ | $1.2 \times 10^{-1}$ | 3.5 | 2.4 | $8 \times 19^{-2}$ | $3.5 \times 10^{-2}$ | $5.4 \times 10^{-1}$ | $4 \times 10^{-1}$ |
| nOnc | $8 \times 10^{-3}$ | $1.5 \times 10^{-2}$ | 16.4 | $9.2 \times 10^{-1}$ | $1.1 \times 10^{-3}$ | $4 \times 10^{-4}$ | $3 \times 10^{-4}$ | $1.7 \times 10^{-4}$ |

Relative $k_{cat}$ for C > p CpA and UpG and relative $V_{max}/[Eo]$ for long-chain substrates were calculated.
[a]Sodium acetate 0.2M (pH 5.5)
[b]Tris 0.1M (pH 7.5) NaCl 0.1M.

The Onc activity towards C>p is dramatically reduced as compared to that of pancreatic RNases. Activity towards cyclic phosphate mononucleotides C>p or U>p was not been detected for eosinophil derived neurotoxin (EDN), eosinophil cationic protein (ECP) or angiogenin (Shapiro et al., *Biochemistry* 25: 3527–3532 (1986); Sorrentino & Glitz, *FEBS* 288: 23–26 (1991); Sorentino et al., *J. Biol. Chem.* 267: 14859–14865 (1992)). This reduction in efficiency of the hydrolysis step of RNase catalytic mechanism has been attributed mainly to substitutions of the aromatic side-chain of Phe120 (Harper et al., *Proc. Natl. Acad. Sci. USA* 85:7139–7143 (1988); deMel et al., *J. Biol. Chem.* 267: 247–256 (1994); Sorrentino & Libonati, *Arch. Biochem. Biophys.* 312:340–348 (1994)). Human angiogenin, ECP and EDN have a Leu residue at this position, but Onc has conserved the Phe residue. The reduction in Onc activity of the hydrolysis step in relation to the transphosphorylation step, however, seems to be lower than for other non-pancreatic RNases.

We have not found any important differences in the relative catalytic activity at pH 5.5 or 7.5. However, absolute kcat values are higher at pH 5.5 for Onc and at pH 7.5 for RNase A and hRNase. Ardelt et al. (*Protein Science* 3, Suppl. 1, 137 (Abst. 486) (1994)) found an optimal activity for Onc around pH 5.5. Sorrentino & Libonati (1994) reported a shift to lower pH optimal for human nonpancreatic RNases relative to human pancreatic RNase.

TABLE 2

Ratio of substrate cleavage for hRNase. Onc and Onc-hRNase hybrids.[a]

| | Poly(C)/poly(U) |
| --- | --- |
| RNaseA | 11 |
| rhRNase | 16 |
| rOnc$_{1-9}$-hRNase$_{12-127}$ | 4 |
| rhRNase$_{1-11}$-Onc$_{12-127}$ | 1.5 |
| nOnc | 0.04 |

[a]The ratio is calculated from absolute Vmax/[Eo]. Assay performed in sodium acetate 0.2M, pH 5.5 at 25° C.

The role of the N-terminal region was also studied in the "reflecting" mutant, rhRNase$_{1-11}$-Onc$_{10-104}$. By substituting the first 9 amino acids of Onc with residues 1–11 of hRNase, there is an increase of activity, from 2 to 90 fold depending on the substrate assayed, in relation to Onc. The increase in catalytic efficiency is more pronounced for poly(C), and the enzyme shows a slight preference for poly(C). Interestingly, the hRNase$_{1-11}$Onc$_{10-104}$ hybrid is much more active against C>p, CpA and poly(C), but is less efficient with UpG substrate in relation to Onc.

Onc does not display inhibition by poly (U) as observed for the other RNases we studied. In the substrate range 0.05 to 1.5 mg/ml we have found a pronounced inhibition of activity by poly(U) concentrations above 0.2–0.4 mg/ml for RNase A and hRNase, and for both hybrids (rhRNase1-11-Onc 10–104, $rOnc_{1-9}$-$hRNase_{12-127}$), whereas Onc does not show a substrate inhibition. An inhibition by high poly(U) substrate concentration has been described for RNase A (Irie et al., *J. Biochem.* (Tokyo) 100:1057–1063 (1984)). The kinetic results presented indicate that the N-terminal region contributes to the catalytic efficiency and substrate specificity.

We observed that Onc and hRNase had different responses to changes in ionic strength. We therefore compared the influence of ionic strength on catalytic activity of RNase A, rhRNase, Onc and the hybrid proteins. A comparison was made of the relative enzyme activity curves of these proteins as a function of NaCl concentration. With increasing ionic strength, enzyme activity is initially enhanced for all proteins, reaching an optimum. The optimum activity is shifted to higher salt concentrations for human pancreatic RNase relative to bovine RNase A, and for both pancreatic RNases relative to Onc. The hybrids $rOnc_{1-9}$-$hRNase_{12-127}$ and $rhRNase_{1-11}$-$Onc_{10-104}$ show a pattern very similar to that of rhRNase, with a maximum activity around 100 mM NaCl. However, the curve of both Onc-hRNase hybrids is slightly biphasic. The Onc mutant (K9Q), like Onc, decreased dramatically in activity from 10 mM to 150 mM. The decrease in activity above the optimal concentration of NaCl is much more pronounced for Onc and the rOnc(K9Q) than for pancreatic RNases or either of the RNase hybrids.

The Pyr-1, Leu-23 rOnc was compared with Met(–1)-rOnc, and Met(–1), Gln1, Leu23 rOnc, and native Onc for activity against poly(U) and UpG (Table 3).

TABLE 3

Relative activity (%) of Met-1 rOnc (Q1, M23L) and rOnc (<E1, M23L) in relation to native Onc (nOnc)[a]

|  | Poly(U) | UpG |
| --- | --- | --- |
| nOnc | 100 | 100 |
| Met-1-rOnc (Q1, M23L) | 20 | 12 |
| rOnc (<E1, M23L) | 170 | 190 |

[a]Assay performed in sodium acetate 0.2 M, pH 5.5 at 25° C.

Recombinant Onc (<E1, M23L) was approximately 6 fold more active than the same uncleaved (Met–1) form of the protein (rOnc (Q1, M23L) and it was slightly more active than native Onc. Thus, formation of the pyroglutamyl residue increased specific activity indicating an important role of this amino acid in catalysis. The uncleaved protein, Met(–1), Gln1, Leu23 mutant was about 2-fold more active against poly(U) and RNA than the recombinant Met(–1), Glu1 Onc. This increase may be due to the Met23 to Leu substitution. Met23 is conserved in all the RNase A homologues, however Met3o to Leu substitution has been found not to affect the catalytic activity of angiogenin. Shapiro et al., *Anal. Biochem.* 175:450–461 (1988).

The recovery of fully active Onc by the cleavage of Met(–1) residue experimentally demonstrates a role for pyrglutamate at the amino terminal end (pyr1) suggested from comparing the native and recombinant Onc crystallographic data. Cleaved rOnc recovers the specific activity of native Onc against UpG. Recombinant Onc (K9Q) shows a decrease in enzyme activity of about 2-fold relative to rOnc with RNA or poly (U), consistent with the involvement of Lys9 and the pyroglutamyl residue in the active site configuration (Mosimann et al., *J. Mol. Biol.* 236: 1141–1153 (1994)).

In sum, recombinant Met(–1)-hRNase was fully active, indistinguishable in specific activity, or substrate specificity from the native, human derived, hRNase (Sorrentino & Libonati, 1994). In contrast to rhRNase, Met(–1)-rOnc was found to have only ¹⁄₁₀th the activity for RNA and ¹⁄₃₀th for poly (U) in relation to native Onc. Since the recombinant proteins were expressed with a formylmethionine at the N-terminus the low activity of the rOnc suggested that the pyroglutamyl residue may play an important role in enzyme activity.

EXAMPLE V

This example describes the substrate preference of rOnc, rhRNase, and hybrid proteins.

RNA specificity of the recombinant proteins rOnc, rhRNase, rOnc mutant (K9Q) and rOnc-hRNase hybrids in reticulocytes was tested by using rabbit reticulocyte lysate. Enzymes, at concentrations of 1, 10, 100 nM, and rabbit reticulocyte lysates were incubated for 15 minutes at 30° C. After incubation, the total RNA was isolated from the reticulocyte lysates using the RNAzol TM method supplied by TEL-TEST INC. Total RNA was analyzed on 10% polyacrylamide gels containing 7.5 M urea. In certain circumstances the rabbit reticulocyte lysate was pretreated with N-ethylmaleimide.

We have previously found that certain members of the RNase A superfamily have selectivity for tRNA within Xenopus oocytes or reticulocyte lysates (Saxena et al., *J. Biol. Chem.* 266: 21208–21214 (1992); Rybak et al., *J. Biol. Chem.* 266:21202–21207 (1991)). Since Onc selectively cleaves tRNA and hRNase does not, we examined the RNA specificity of the hybrid Onc-hRNase proteins. Aliquots of total cellular RNA in rabbit reticulocyte lysates were incubated for 15 min with 1, 10, and 100 nM concentrations of Onc, hRNase and the mutant and hybrid proteins. Total RNA was isolated and analyzed over 10% polyacrylamide gels containing 7.5 M urea.

The results indicate that Onc is very specific for tRNA whereas hRNase degrades ribosomal RNAs at the same concentration as tRNAs. Examining the specificity of $rhRNase_{1-11}$-$Onc_{10-104}$ shows that it retains the tRNA selectivity of Onc yet at a much reduced overall enzyme activity. This differs markedly from the results obtained for common pancreatic RNase substrates in sodium acetate 0.2 M, pH 5.5 buffer, where this hybrid had increased activity compared to Onc (Table 1). For the $rOnc_{1-9}$-$hRNase_{12-127}$ hybrid, the tRNA specificity is lost and the hybrid resembles hRNase. Thus the tRNA specificity domain resides outside the N-terminal region. The rOnc retained the tRNA specificity but at a reduced overall enzymatic activity in relation to native Onc, and K9Q mutant showed the same degradation pattern as recombinant Onc but less efficiently. The possibility existed that ribonuclease inhibitor (RI) in the reticulocyte lysate was differentially inhibiting the activities or specificities of these RNases. Therefore, reticulocyte lysates were pretreated with N-ethylmaleimide to inactivate RI and the potency and specificity of the above RNases was examined. Indeed, the potency of hRNase and $rOnc_{1-9}$-$hRNase_{10-127}$ was slightly increased in the RI depleted reticulocyte lysates whereas the Onc and $rhRNase_{1-11}$-$Onc_{10-104}$ hybrid were not, as one would expect from their relative sensitivities to RI. Thus, the N-terminus does not define the tRNA specific activity of Onc.

Onc shows a greatly decreased specific activity towards common pancreatic RNase substrates in relation to RNase A, and a substrate preference for uridine in the 5' base position (B1 site) in relation to the cleavage site and guanosine for the base in the 3' position (B2 site) (Ardelt et al., 1994). Our results also indicate a clear preference for UpG relative to CpA (Table 1). Depending on the substrate assayed, Onc activity is between $10^{-4}$ to 16% in relation to hRNase. Onc activity is higher for RNA or poly(U) than that for poly(C) while hRNase and RNase A are more active with poly(C) (Table 2). Onc clearly prefers poly(U) and RNA, as described for other nonpancreatic type members in the RNase family (Beintema et al., *Prog. Biophys. Molec. Biol.* 51:165–192 (1988); Sorrentino & Libonati, 1994), whereas pancreatic RNases (Beintema et al., 1988; Sorrentino & Libonati, 1994), show a distinct preference for poly (C).

EXAMPLE VI

This example describes ribonuclease inhibitor interaction.

Steady-state inhibition constants ($K_i$) for PRI interaction were determined using a modification of a method (Vincentini et al., *Biochemistry* 29:8827–8834 (1990)) to analyse competitive slow tight-binding inhibition mechanisms. Steady-state rates of product formation were calculated by a spectrophotometric method. 1.7mM CpA for RNase A, rhRNase and $rOnc_{1-9}$-$hRNase_{12-127}$, or UpG for Onc and $rhRNase_{1-11}$-$Onc_{10-104}$, were used as substrate and the reaction was performed at 25° C. in 50 mM MES-NaOH, pH 6, 125 mM NaCl, 1 mM EDTA, 1.2 mM DTT, 0.1% poly(ethylene glycol) and 0.2 mg/ml BSA. The reaction was started by the addition of enzyme (0.01 to 2 nM depending on the assayed protein) and followed during 90–120 min. Several inhibitor concentrations were distributed below and above the enzyme concentration. For Onc and $rhRNase_{1-11}$-$Onc_{10-104}$, the inhibitor concentration was increased well above enzyme concentration to achieve inhibition. The amount of product formed was calculated by following the absorbance decrease at 286 nm for CpA (change in $\epsilon=521$ $M^{-1}$ $cm^{-1}$) and at 280 nm for UpG (change in $\epsilon=757$ $M^{-1}$ $cm^{-1}$). The calculated steady-state rates for each inhibitor concentration were fitted by nonlinear regression to the equation for tight binding inhibition as described by Vicentini et al. (1990). In each case $I_{50}$, defined as the total inhibitor concentration required to give 50% inhibition, were deduced from the $V_s$–I Dixon plot and compared to the calculated $K_i$, considering in each case the total enzyme concentration.

We have analyzed the apparent second-order rate constant for the association of placental ribonuclease inhibitor with Onc, rhRNase and the two hybrid RNases by studying the competition between these proteins and RNase A or angiogenin. The $K_i$ values are summarized in Table 4.

TABLE 4

Dissociation constant for the inhibition of RNases by PRI.

| | $K_i^a$ (M) |
|---|---|
| RNaseA | $5.8 \times 10^{-14}$ |
| rhRNase | $2.0 \times 10^{-13}$ |
| $rOnc_{1-9}$-$hRNase_{12-127}$ | $5.6 \times 10^{-12}$ |
| $rhRNase_{1-11}$-$Onc_{10-104}^b$ | $\geq 4 \times 10^{-7}$ |
| $nOnc^b$ | $\geq 1 \times 10^{-6}$ |

[a]$K_i$ values were calculated from the observed steady-state rates ($v_s$) at different inhibitor concentrations, by fitting the data to the tight-binding nonlinear regression equation.
[b]For Onc and $rhRNase_{1-11}$-$Onc_{10-104}$, approximate $K_i$ was directly calculated from the $I_{50}$ values, considering the enzyme concentration used.

RNase A was used a control and the value obtained is similar to that previously reported to that (Lee et al., 1989). Recombinant hRNase has a $K_i$ similar to that of RNase and Onc has a dramtically lower inhibitor affinity.

The hybrid protein ($rOnc_{1-9}$-$hRNase_{10-127}$) has about 30×increased $K_i$ in relation to rhRNase, suggesting that residues 1–11 of hRNase contributes to RI interaction. The region includes residues Lys-7 and Gln-11, sites where RNase A interacts with the inhibitor (Kobe & Deisenhofer, *Nature* 374:183–186 (1995)). Neumann & Hofsteenge (*Protein Science* 3:248–256 (1994)) have reported that ionic interactions of Lys-7, and to a minor extent Lys-1, of RNase A, contribute to pig ribonuclease inhibitor binding. However, in the Onc N-termius Lys-9 may partially replace Lys-7 interaction. The N-terminal a helix of angiogenin is also reported to be involved in RI interaction; elimination of one positive residue (Arg-5 → Ala) decreased affinity for PRI by 50 fold (Shapiro & Vallee, *Biochemistry* 31:12477–12485 (1993)). The replacement of residues 8–22 of angiogenin with-7–21 of RNase A increased its affinity for PRI (Bond & Vallee, *Biochemistry* 29:3341–3349 (1990)) and this angiogenin/RNase A hybrid had a lower capacity of in vitro protein synthesis inhibition but a higher angiogenic activity.

Replacement of residues 1–9 of Onc by residues 1–11 of hRNase ($rhRNase_{1-11}$-$Onc_{10-104}$ hybrid) causes about 3-fold increase of PRI affinity in relation to Onc. The range of inhibitor concentration of Onc and $rhRNase_{1-11}$-$Onc_{10-104}$ is far from the 1:1 enzyme to inhibitor stoichiometry characteristic of the tight-binding mechanism. The given approximate $K_i$ constants were deduced from the observed $I_{50}$. The extremely low PRI affinity and the intrinsic limitations of the assay conditions, did not allow reaching total activity inhibition. Thus, their $K_i$ values cannot be accurately calculated in the described assayed conditions.

One intriguing feature of Onc that may relate to its cytotoxicity is its relative insensitivity to RNase inhibitor. Wu et al., *J. Biol. Chem.* 268:10886–10693 (1993). Onc is enzymatically less active than hRNase but it is more RI resistant and more cytotoxic. Another cytotoxic RNase with antitumor activity, bovine seminal RNase (D'Alessio, *Cell Biology* 3:106–109 (1993)) also has unusual RI sensitivity. RI binds tightly to the monomeric form but not to the dimeric, biologically active form (Tamburrini et al., *Eur. J. Biochem.* 190:145–148 (1990); Murthy & Sirdeshmukh, *Biochem. J.* 281:343–348 (1992); Kim et al., *J. Biol. Chem.* 270:10525–10530 (1995)). Moreover, artificial dimers of RNase A acquire antitumor activity and are RI resistant (Donato et al., *J. Biol. Chem.* 269:17394–17396 (1994); Kim et al., 1995). RI may normally protect cells from potentially cytotoxic endogeneous RNases. PRI has been found to inhibit most mammalian members of RNase A family. However, amphibian RNases are not inhibited by mammalian PRI, and mammalian RNases are reported to be insensitive to the amphibian counterpart to PRI (Kraft & Shortman, *Biochim. Biophys. Acta.* 217:164–175 (1970)). RNase inhibitors have been detected in most tissues in mammalian, in other vertebrates (Blackburn & Moore, "Pancreatic ribonucleases" in *The Enzymes*. (Boyer, P. D., ed), 15 pp. 317–433, Academic Press, N.Y. (1982)) and in insects (Garcia-Segura et al., *Biochim. Biophys. Acta.* 826:129–136 (1985)).

EXAMPLE VII

This example describes the protein synthesis assay in the presence of retinoic acid as a measure of cytotoxicity.

U251 or 9L (rat glioma) cells were grown in Dulbecco's modified Eagle's medium (DMEM) containing 10% fetal calf serum, 2 mM glutamine, 1 mM sodium pyruvate, 0.1 mM non-essential amino acids, and 10 mg/ml gentamycin. Protein synthesis inhibition by RNases were determined as described previously (Wu et al., 1995). Briefly, cells in 100 $\mu$l were plated at concentrations of $1-2\times10^5$ cells/ml in 96-well microwell plates overnight in DMEM complete medium. Retinoic acid (Calbiochem) (15 mM in dimethyl sulfoxide, DMSO) stock solution was diluted into leucine-free RPMI 1640 medium (Biofluids) without fetal calf serum to 10 mM. The same dilution of DMSO was added in the control solutions. After removing the complete DMEM medium, cells were incubated in the above leucine-free RPMI 1640 medium containing increasing concentrations of ribonucleases with or without retinoic acid for 16 h followed by a 1 h pulse with 0.1 mCi [14C]-leucine. Cells were harvested onto glass fiber filters using a PHD cell harvester, washed with water, dried with ethanol, and counted. The results were expressed as the percentage of [14C]-leucine incorporation in mock-treated control cells.

Reconstituting the N-terminal pyroglutamyl residue increases rOnc enzyme activity and cytotoxicity (Table 5).

TABLE 5

Cytotoxicity of Met-1 rOnc (Q1, M23L) and rOnc (<E1, M23L) in relation to nOnc

|  | Protein synthesis (%) [a] | Relative IC$_{50}$ (%) [b] |
|---|---|---|
| nOnc | 9.5 | 100 |
| Met-1-rOnc (Q1, M23L) | 38.5 | 4.3 |
| rOnc (<E1, M23L) | 10.7 | 33.3 |

[a] % of protein synthesis at $10^{-6}$M of enzyme concentration relative to untreated control
[b] Relative amounts of enzyme that corresponds to 50% inhibition compared to native Onc.

To further examine the relationship between enzyme activity and cytotoxicity and to try to dissect the domains of Onc that differ from hRNase that impart cytotoxicity, we have examined the toxicity of the onc-hRNase hybrids. In the presence of retinoic acid, rhRNase lacked cytotoxicity from $10^{-7}$ to $10^{-5}$ M, whereas Onc at the same concentration completely blocked U251 cell protein synthesis. This may be explained by the fact that Onc is practically insensitive to RI. In order to further test this hypothesis we assayed the cytotoxicity of two other ribonucleases that have different affinities for RI, rOnc$_{1-9}$-hRNase$_{12-127}$ and rhRNase$_{1-11}$-Onc$_{10-104}$ hybrids. Although both ribonucleases are enzymatically less active than rhRNase, they are at least 100 times more toxic than rhRNase. These results further support the proposal that RI sensitivity plays an important role in ribonuclease cytotoxicity although other, as yet undetermined factors such as binding, cell entry or degradation, also appear to play some role.

EXAMPLE VIII

This Examples demonstrates the inhibition of HIV-1 replication by Onc.

Onc was purified from frog eggs as previously discussed. Recombinant RNases were constructed, expressed and purified as reported above. CD4-positive H9 lymphocyte cells persistently infected with HIV-1 IIIB strain and the MN strain of HIV-1 were obtained from Dr. Robert Gallo, National Cancer Institute, NIH, Bethesda, Md. H9 cells (ATCC No. HTB 176) were also persistently infected with the MN strain of HIV-1 and U937 cells (ATCC No. CRL 1593) were persistently infected with either the IIIB strain or the MN strain of HIV-1. These cells were grown in RPMI-1640 medium with 10% heat-inactivated fetal bovine serum and 50 $\mu$g/ml gentamycin. Prior to use in Onc inhibition studies, persistently infected H9 cells were washed extensively to reduce levels of free virus and resuspended at $2\times10^5$ cells/ml for use in experimental protocols. Either $1\times10^{-8}$ or $5\times10^{-8}$ M Onc was added to washed cells and cultures were sampled daily over a 5 day period. After the incubation, cells and medium were harvested by centrifuging the culture at 400×g for 10 min. The supernatant medium was filtered through a 0.45-mm-pore size membrane, aliquoted, quickly frozen and stored at −70° C. Cell pellets were processed to analyze RNA and the supernatant was used to determine p24 antigen levels. The p24 antigen concentrations were determined by quantitative HIV-1 p24 antigen capture EIA performed according to kit specifications (Coulter).

Growth of normal H9 and U937 cells were determined in the presence of Onc up to 3 days. Each initial 50 ml culture had $2\times10^5$ cells/ml and viability was determined by trypan blue exclusion. $1\times10^7$ H9 cells (cultured in 75 cm$^2$ flasks) were incubated with $1\times10^{-8}$ M and $5\times10^{-8}$ M Onc for 5 days. Each day one flask of cells was processed as follows to analyze the RNA. Total RNA was extracted using RNA-zol™ according to the protocol supplied by Tel-Test Inc., Friendswood, Tex. Northern blot analysis was carried out according to protocols described in Maniatis et al., *Molecular Cloning: A laboratory manual, Cold Spring Harbor, N.Y.: Cold Spring Harbor Laboratory* (1982)). Briefly approximately 1.5 $\mu$g of total RNA from each set was denatured for 15 min. at 55° C. in 20 $\mu$l of [20 mM morpholinopropane sulfonic acid-NaOH (pH 7.0) containing 5 mM sodium acetate and 1 mM EDTA (pH 8.0), 50% formamide, and 6.5% formaldehyde] and 2 $\mu$l RNA sample buffer [50% glycerol, 1 mM EDTA (pH 8.0), 0.25% bromophenol blue, and 0.25% xylene cyanol] and a small amount of ethidium bromide. These samples were electrophoresed on a denaturing 1.4% agarose gel containing 6.7% formaldehyde and 1× MOPS buffer [20 mM morpholinopropane sulfonic acid-NaOH (pH 7.0) containing 5 mM sodium acetate and 1 mM EDTA (pH 8.0)] at 100 V for 3–4 hr. The gels were equilibrated in 20×SSC [3M NaCl, 0.3M sodium citrate, pH 7.0] for 45 min before overnight capillary blotting onto Nytran Plus membranes .(Schleicher & Schuell) in 10×SSC. RNA was fixed on to filters by UV cross-linking (UV Stratalinker; Stratagene, LaJolla, Calif.). Prehybridization was carried out at 42° C. for 6 h in hybridization buffer [0.2% polyvinyl-pyrrolidone (MW 40,000), 0.2% ficoll (MW 400,000), 0.2% BSA, 0.05M Tris-HCl, pH 7.5, 1M sodium chloride, 0.1% sodium pyrophosphate, 1% SDS, 10% dextran sulfate (MW 500,000) and denatured salmon sperm DNA (0.1 mg/ml). Following prehybridization, hybridization was carried out for 20 h at 42° C. using the $^{32}$P-Nick translated ([$\alpha$-$^{32}$P]-dCTP; DuPont, NEN) HIV-1 specific ~8 kb DNA probe (AvaI digested 8,088-bp DNA fragment of pNL4-3;) (13). The blot was washed twice in 2×SSC/1% SDS at room temperature for 15 min each and once in 0.2×SSC/1% SDS at 65° C. for 30 min. Autoradiography was carried out with intensifying screens at −70° C. and developed by X-Omat (Kodak).

The addition of onc to cells blocked p24 production from chronically HIV-1$_{IIIB}$ infected H9 cells. Onc at $1\times10^{-8}$ M completely blocked p24 antigen production for two days and $5\times10^8$ M Onc completely blocked p24 antigen production for at least 5 days. In H9 cells chronically infected with another strain of HIV-1, MN (Gallo et al., *Science* 224:500–503 (1984)), Onc at the same concentration inhibited HIV-1 production 60% to 75% over a 5 day period. We also studied U937 cells persistently infected with these two HIV-1 strains (IIIB and MN) and found Onc also inhibited p24 antigen production of both strains. The mammalian cells were persistently infected with HIV indicating that steps in the HIV-1 lifecycle subsequent to genomic integration are susceptible to ribonuclease intervention.

Although Onc was not cytotoxic to H9 cells below $1\times10^{-7}$M (Youle et al., *Proc. Natl. Acad. Sci. USA* 91:6012–6016 (1994)) we examined whether Onc in the $10^{-8}$ M concentration range slowed the rate of cell division in H9 cells and U937 cells. At $5\times10^{-8}$ M, Onc was not cytotoxic to cells and only slightly inhibited the H9 cell growth rate and did not affect U937 cell growth rate. Therefore, Onc directly inhibits HIV-1 production within viable and dividing cells.

To investigate the molecular basis of RNase anti-viral action leading to the reduction in HIV p24 antigen, the levels of HIV-1 RNA at various times during exposure to Onc were analyzed. Northern blot analysis of the total RNA from uninfected H9 cells and chronically HIV-1$_{IIIB}$ infected H9 cells treated with different doses of Onc showed that Onc caused a large decrease in the levels of all the HIV-1 RNA transcripts. The higher molecular weight HIV-1 transcripts were most susceptible to Onc. Onc at 20–100 fold higher doses ($1\times10^{-6}$ to $1\times10^{-5}$ M) can enter the cell cytosol in great enough amounts to degrade cellular RNA (Wu et al., *J. Biol. Chem.* 268:10686–10693 (1993)). However, the experiments provide the first evidence that an RNase at one one-hundredth the cytotoxic concentration can actually enter cells and degrade viral RNA species. Consistent with this model are recent results showing that disruption of intracellular traffic through the Golgi apparatus can greatly increase the delivery of Onc to the cytosol (Wu et al., *J. Biol. Chem.* 270:7476–17481 (1995); Wu et al., *J. Cell. Biol.* 125:743–53 (1994)). The most dramatic decrease in HIV-1 RNA levels occurred with $5\times10^{-8}$ M Onc and lasted up to 4 days. After 4 days of exposure to the initial Onc dose, HIV-1 RNA levels began to increase. This increase in HIV-1 RNA level after 4 days of inhibition precedes the increase in p24 antigen concentrations. The Onc treatment at $1\times10^{-8}$ M resulted in a similar inhibition of HIV-1 RNA levels although the inhibition at this lower dose of Onc was shorter in duration than for the $5\times10^{-8}$ M Onc treated cells. This may reflect the half life of Onc within cultured cells. When cells were treated with $1\times10^{-8}$M Onc the eventual reappearance of the HIV-1 RNA after 3 days corresponded with renewed p24 antigen production. These results also show that the ribonuclease is not lethal to the cells as they re-express HIV-1 RNA and p24 antigen with increased time after ribonuclease exposure.

Because of the eventual resynthesis of HIV-1 RNA, we added a second dose of Onc at $1\times10^{-8}$ M, two days after an initial onc treatment at $1\times10^{-8}$ M on day zero. The second dose of Onc caused a significant further decrease in p24 antigen production and in cell division rate. However, the inhibition of p24 antigen by the second treatment was less than that of the first exposure to Onc. Comparing the RNA from H9 cells treated on day 0 only and those treated at day 0 and day 2 with $1\times10^{-8}$ M Onc revealed that the increase in HIV-1 RNA levels seen 4 and 5 days after a single inoculum of Onc was blocked by the second addition of Onc. Thus, repeated application of ribonucleases has repeated antiviral effects.

We also compared HIV-1 infectivity titers on virus harvested from Onc treated H9 cells and untreated controls. Titers of virus from Onc treated and untreated cells standardized for the same amount of p24 antigen showed no relative difference in infectivity. Thus, the virus eventually produced by Onc treated cells was not defective.

Examining the ribosomal RNA from the same H9 cell samples where viral RNA was destroyed showed no effect of Onc on rRNA. We also examined the levels of messenger RNAs encoding human actin, glyceraldehyde-3-phosphate dehydrogenase and the transferrin receptor in $5\times10^{-8}$M Onc treated and control H9 cells. No decrease in mRNA levels was found in three out of the three mRNAs examined. Thus Onc expressed a surprising selectivity for HIV-1 RNA species within cells, a finding consistent with its low cytotoxicity and minor effect on cell growth rate. However, tRNA may be also highly susceptible to degradation by onc and certain homologous RNases (Lin et al., *Biochem. Biophys. Res. Comm.* 204:156–162 (1994); Saxena et al., *J. Biol. Chem.* 267:21982–21986 (1992)). As Onc is not likely to express sequence specificity for HIV RNA, perhaps proteins complexed with RNA protect endogenous cellular RNAs from Onc to a greater extent than the HIV-1 RNAs.

Previously it was found that human eosinophil derived neurotoxin and bovine pancreatic RNase A, both members of the ribonuclease family homologous to Onc in sequence, lacked antiviral activity. Youle et al. (1994). As previously discussed, several recombinant forms of Onc were constructed (Boix et al., *J. Mol. Biol.* in press (1996)) and used these variants to probe the structural differences between human pancreatic RNase and Onc that generate antiviral activity. As noted previously, when rOnc was expressed with an N-terminal methionine instead of the pyroglutamyl residue found in the native frog protein, ribonuclease activity was decreased 80–90%. We compared the antiviral activity of native Onc, recombinant Onc expressed with an N-terminal methionine residue and recombinant Onc treated with cyanogen bromide to reconstitute the N-terminal pyroglutamyl residue. The experiments showed that, whereas native Onc and the recombinant pyroglutamyl form of Onc expressed potent antiviral activity, the N-terminal methionine form of Onc completely lacked activity. Thus antiviral activity correlates with the degree of ribonuclease activity as the two pyroglutamyl forms of onc are more active in both respects than the N-terminal methionine form. When the N-terminal 11 amino acid residues of human RNase are exchanged for the N-terminal 9 amino acids of Onc the chimera expresses greater enzyme activity than native or recombinant Onc. However, when antiviral activity is analyzed the human RNase/Onc chimera lacks antiviral activity. Thus, although ribonuclease activity appears to be required for antiviral activity, it is not sufficient and some feature in the N-terminal 9 amino acids beyond RNase activity appears essential for the antiviral effect.

All publications and patents mentioned in this specification are herein incorporated by reference into the specification to the same extent as if each individual publication or patent was specifically and individually indicated to be incorporated herein by reference.

What is claimed is:

1. An isolated nucleic acid molecule encoding a recombinant ribonuclease from *Rana pipiens* oocytes (rOnc protein), comprising:

a polypeptide of SEQ ID NO: 1 having a glutamine residue at position 1, a hydrophobic residue other than methionine at position 23, a lysine at position 9, a histidine at position 10, a histidine at position 97, a lysine at position 31, a phenylalanine at position 98, and a threonine at position 35, and no more than a single conservative amino acid substitution an other than positions 1, 9, 10, 23, 31, 35 and 98, wherein the conservative amino acid substitution does not introduce a methionine into the polypeptide; and a methionine at position −1 that can be subsequently cleaved to allow cyclization of the glutamine residue at position 1 to form a pyroglutamyl residue, such that the resulting protein is ribonucleolytic and cytotoxic.

2. The nucleic acid of claim 1, wherein the nucleic acid encodes a polypeptide having a leucine at position 23.

3. A method of making a rOnc protein comprising:

i. expressing in a host cell the nucleic acid molecule of claim 1;

ii. cleaving the amino terminal methionine with a cleaving agent; and iii. causing the glutamine residue at position 1 to cyclize to a pyroglutamyl residue.

4. The method of claim 3, wherein the nucleic acid encodes a leucine at position 23.

5. The method of claim 3, where the cleaving agent is a peptidase or cyanogen bromide.

6. A host cell that expresses the nucleic acid molecule of claim 1.

7. An expression vector comprising the nucleic acid molecule of claim 1.

8. The expression vector of claim 7, wherein the polypeptide has a leucine at position 23.

* * * * *

UNITED STATES PATENT AND TRADEMARK OFFICE
CERTIFICATE OF CORRECTION

PATENT NO. : 6,649,393 B1
DATED : November 18, 2003
INVENTOR(S) : Youle et al.

It is certified that error appears in the above-identified patent and that said Letters Patent is hereby corrected as shown below:

Title page,
Item [56], References Cited, OTHER PUBLICATIONS, under "*Creighton, T.E.*," reference, "pp. 9,62&63" should read -- pp. 9, 62 & 63 --.

Column 4,
Line 14, "similar-amino" should read -- similar amino --.

Column 6,
Line 22, "85i" should read -- 85% --.

Column 7,
Line 3, "may-be" should read -- may be --.

Column 11,
Line 57, "an. rOnc" should read -- an rOnc --.
Line 64, ""linkers"" should read -- "linkers" --.

Column 13,
Lines 37 and 38, "hRNase$_{12\text{-}127}$hybrid" should read -- hRNase$_{12\text{-}127}$hybrid --.

Column 14,
Line 2, "1=8.8)" should read -- 1%=8.8) --.
Line 32, "ionization:(MALDI)" should read -- ionization (MALDI) --.

Column 15,
Line 3, "hRNase$_{2\text{-}127}$" should read -- hRNase$_{12\text{-}127}$ --.

Column 22,
Line 44, "membranes .(Schleicher" should read -- membranes (Schleicher --.
Line 61, "onc" should read -- Onc --.
Line 64, "5x10$^8$" should read -- 5x10$^{-8}$ --.

UNITED STATES PATENT AND TRADEMARK OFFICE
CERTIFICATE OF CORRECTION

PATENT NO.    : 6,649,393 B1
DATED         : November 18, 2003
INVENTOR(S)   : Youle et al.

It is certified that error appears in the above-identified patent and that said Letters Patent is hereby corrected as shown below:

<u>Column 24,</u>
Lines 17 and 49, "onc" should read -- Onc --.

Signed and Sealed this

Second Day of March, 2004

JON W. DUDAS
*Acting Director of the United States Patent and Trademark Office*